United States Patent
Guillonneau et al.

[11] Patent Number: 5,958,938
[45] Date of Patent: Sep. 28, 1999

[54] BIS-PYRIDO[4,3-B]CARBAZOLE COMPOUNDS

[75] Inventors: Claude Guillonneau, Clamart; Yves Charton, Sceaux; Ghanem Atassi, Saint Cloud; Alain Pierre, Les Alluets le Roi; Nicolas Guilbaud, La Celle Saint Cloud, all of France

[73] Assignee: Adir et Compagnie, Courbevoie, France

[21] Appl. No.: 09/120,899

[22] Filed: Jul. 22, 1998

[30] Foreign Application Priority Data

Aug. 6, 1997 [FR] France ................. 97 10066

[51] Int. Cl.⁶ .................. A61K 31/435; C07D 471/04
[52] U.S. Cl. .................................. 514/285; 546/70
[58] Field of Search ................. 546/70; 514/285

[56] References Cited

U.S. PATENT DOCUMENTS 5,407,940  4/1995  Bisagni et al. .................... 514/285

*Primary Examiner*—Patricia L. Morris
*Attorney, Agent, or Firm*—The Firm of Gordon W. Hueschen

[57] ABSTRACT

Compounds of the formula:

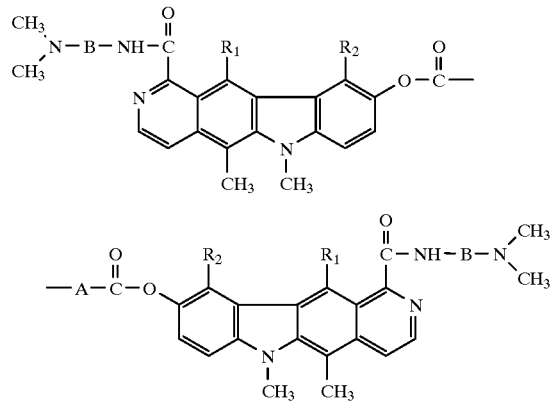

in which $R_1$, $R_2$, A and B are as defined in the description, their optical isomers, N-oxides and addition salts with a phar-maceutically acceptable acid, and their use as anti-tumor agents.

6 Claims, No Drawings

BIS-PYRIDO[4,3-B]CARBAZOLE COMPOUNDS

The present invention relates to new bis-pyrido[4,3-b] carbazole compounds, to a process for their preparation and to pharmaceutical compositions containing them.

The compounds of the present invention may be used in therapeutics by virtue of their anti-tumor activity.

Certain compounds of the olivacine or ellipticine family are already known for their anti-cancer properties; see patent application EP 0 591 058 A1.

The needs of therapeutics demand the constant development of new anti-cancer agents with the aim of obtaining molecules that are both more active and more specific.

The present invention relates to olivacine or ellipticine compounds that, compared with the closest compounds of the prior art, have novel structures (two identical olivacine or ellipticine groups being linked in the 9-position by means of a dicarboxyalkyl chain), accompanied by excellent anti-tumor activity, especially in the case of resistant solid tumors.

The present invention relates more particularly to:
compounds of formula I:

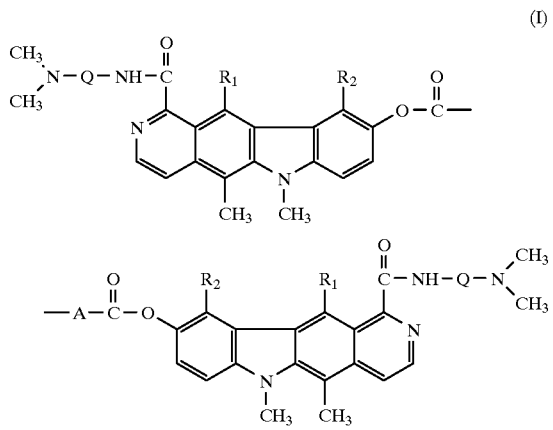

(I)

in which:
$R_1$ and $R_2$, which may be the same or different, each represents a hydrogen atom or a methyl radical;
A represents a linear or branched, saturated hydrocarbon chain containing from 1 to 12 carbon atoms optionally including a hydrocarbon ring having from 3 to 6 carbon atoms;
A may also represent a hydrocarbon ring having from 3 to 6 carbon atoms; and
Q represents a linear or branched hydrocarbon chain containing from 1 to 8 carbon atoms;

as well as their possible optical isomers, N-oxides and addition salts with a pharmaceutically acceptable acid.

The invention relates also to a process for the preparation of compounds of formula I, characterised in that a compound of formula II:

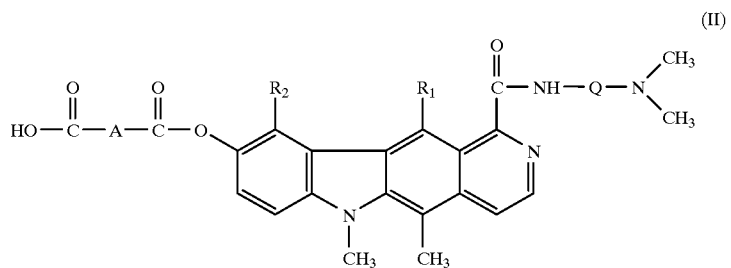

(II)

in which:
$R_1$, $R_2$, A and Q are as defined above, is esterified by a compound of formula III:

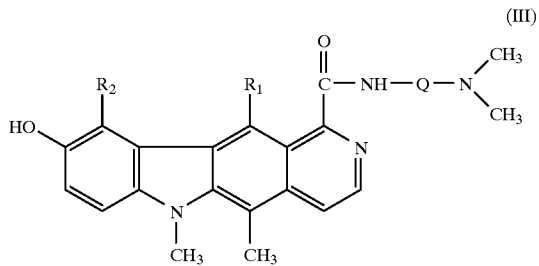

(III)

in which:
$R_1$, $R_2$ and Q are as defined above.

It is especially advantageous to react the compounds of formula II with the compounds of formula III in the presence of a coupling agent such as benzotriazol-1-yloxytripyrrolidinophosphonium hexafluorophosphate and of a tertiary amine such as triethylamine in a polar aprotic solvent such as tetrahydrofuran, dimethylformamide or N-methylpyrrolidone at a temperature of from 0 to 80° C.

The compounds II used as starting materials are described in the French patent application published under No. 2.757.859.

The compounds III used as starting materials are described in patent application EP 0 591 058 A1 or in the French patent application published under No. 2.757.858.

The compounds of formula I yield salts with physiologically tolerable acids, which salts are included as such in the present invention.

Some of the compounds of formula I contain one or more asymmetric carbon atoms and, accordingly, yield enantiomers or diastereoisomers, which likewise form part of the present invention.

The compounds of the present invention have pharmacological properties which are particularly valuable, especially an excellent in vitro cytotoxicity and an in vivo anti-tumor activity which is superior to that of the products of the prior art, which allows them to be used in therapeutics as anti-tumor agents, especially for treating resistant solid tumors.

The present invention relates also to pharmaceutical compositions comprising as active ingredient at least one compound of the present invention, in admixture or in association with one or more pharmaceutical excipients or inert, non-toxic carriers.

The pharmaceutical compositions are generally in dosage unit form suitable for administration orally, rectally or parenterally, and especially in the form of tablets, dragées, gelatin capsules, suppositories and injectable or drinkable solutions.

The dosage varies according to the age and weight of the patient, the route of administration, the nature of the therapeutic indication and any associated treatments, and ranges from 0.1 to 400 mg per day administered in one or more doses. The Examples which follow illustrate the present invention, melting points being determined by means of a capillary tube. The silica used for purification by column chromatography is Amicon silica (0.035–0.07 mm). The pressure used is $10^5$ Pa.

EXAMPLE 1

The bis[1-(2-dimethylaminoethylcarbamoyl)-5,6,11-trimethyl-6H-pyrido[4,3-b]carbazol-9-yl] ester of hexanedloic acid.

5) The bis[1-(2-dimethylaminoethylcarbamoyl)-5,6-dimethyl-6H-pyrido[4,3-b]carbazol-9-yl] ester of 3,3-dimethylpentanedioic acid. M.p. (decomp.)>130° C.

6) The 1-(2-dimethylaminoethylcarbamoyl)-5,6-dimethyl-6H-pyrido[4,3-b]carbazol-9-yl ester of {1-[1-(2-dimethylaminoethylcarbamoyl)-5,6-dimethyl-6H-pyrido[4,3-b]carbazol-9-yloxycarbonylmethyl]cyclohexyl}acetic acid. M.p.: 145–150° C.

7) The bis[1-(2-dimethylaminoethylcarbamoyl)-5,6-dimethyl-6H-pyrido[4,3-b]carbazol-9-yl] ester of 2,2,5,5-tetramethylhexanedioic acid. M.p.: 112–120° C.

8) The bis[1-(2-dimethylaminoethylcarbamoyl)-5,6-dimethyl-6H-pyrido[4,3-b]carbazol-9-yl] ester of cyclohexane-1,4-dicarboxylic acid. M.p. (decomp.)>200° C.

9) The bis[1-(2-dimethylaminoethylcarbamoyl)-5,6-dimethyl-6H-pyrido[4,3-b]carbazol-9-yl] ester of 3-methylpentanedioic acid. M.p.: 115–120° C.

10) The bis[1-(3-dimethylaminopropylcarbamoyl)-5,6-dimethyl-6H-pyrido[4,3-b]carbazol-9-yl] ester of pentanedioic acid and its trihydrochloride, which is an amorphous product.

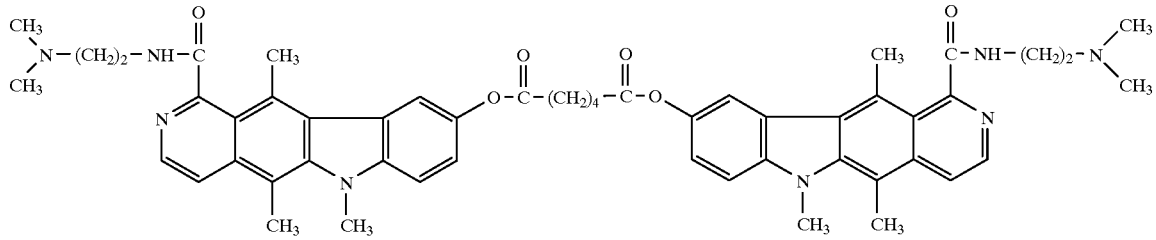

2.6 g of the [1-(2-dimethylaminoethylcarbamoyl)-5,6,11-trimethyl-6H-pyrido[4,3-b]carbazol-9-yl] monoester of hexanedioic acid, 2 g of 9-hydroxy-5,6,11-trimethyl-6H-pyrido[4,3-b]-carbazole-1-carboxylic acid (2-dimethylaminoethyl) amide, 1.23 g of triethylamine and 3.19 g of benzotriazol-1-yloxytripyrrolidinophosphonium hexafluorophosphate are dissolved in 40 ml of N-methylpyrrolidone. The solution is stirred for 24 hours at ambient temperature. Concentration to dryness is carried out. The residue is taken up in a mixture of dichloromethane, an aqueous sodium carbonate solution and the minimum amount of methanol required to dissolve the insoluble material. After being separated off, the oryanic phase is dried over sodium sulphate and concentrated to dryness. The residue is chromatographed on 280 g of silica using, a mixture of dichloromethane, methanol and triethylamine (95/5/0.5) as eluant. The fractions containing the product are concentrated to dryness; the residue is washed with ethanol and dried at 40° C. in vacuo. 1.6 g of the desired product are obtained. M.p.: 220–225° C.

EXAMPLES 2 to 10

By proceeding, as described in Example 1, using the corresponding appropriate obvious starting materials, the compounds of the following Examples have been prepared:

2) The bis[1-(2-dimethylaminoethylcarbamoyl)-5,6-dimethyl-6H-pyrido[4,3-b]carbazol-9-yl] ester of hexanedioic acid. M.p.: 250–254° C.

3) The bis[1-(2-dimethylaminoethylcarbamoyl)-5,6-dimethyl-6H-pyrido[4,3-b]carbazol-9-yl] ester of octanedioic acid (thick gum).

4) The bis[1-(2-dimethylaminoethylcarbamoyl)-5,6,10-trimethyl-6H-pyrido[4,3-b]carbazol-9-yl] ester of hexanedioic acid. M.p.: 260–265° C.

EXAMPLE 11

Pharmacological Study

A/Cytotoxicity study

Three cell lines were used:

1 murine leukaemia, L 1210, 1 murine melanoma, B 16

1 human pulmonary carcinoma, A 549.

The cells are cultured in RPMI 1640 complete culture medium containing 10% foetal calf serum, 2 mM glutamine, 50 units/ml of penicillin, 50 μg/ml of streptomycin and 10 mM Hepes, pH=7.4.

The cells are distributed on microplates and exposed to the cytotoxic compounds. The cells are then incubated for 2 days (L 1210) or 4 days (A 549, B 16). The number of viable cells is then quantified by means of a colorimetric assay, the Microculture Tetrazolium Assay (Carmichael J., DeGraff W. G., Gazdar A. F., Minna J. D. and Mitchell J. R., Evaluation of a tetrazolium-based semiautoimated calorimetric assay : assessment of chemosensitivity testing, Cancer Res., 47, 936–942, 1987).

The results are expressed as $IC_{50}$, the concentration of cytotoxic agent which inhibits the proliferation of the treated cells by 50%. The results obtained for the lines used are shown in the Table below.

Shown below, by way of example, are the results obtained with the compound of Example 1, which is particularly representative of the invention, and two reference products: reference product A being the compound of Example 1 in patent application EP 0 591 058 A1, namely 1-(N,N-dimethylaminoethylaminocarbamoyl)-5,6-diiethyl-9- hydroxy-6H-pyrido-[4,3-b]carbazole, and reference product B being adriamycin (ADR).

| Test compounds | Cytotoxicity IC$_{50}$ (nM) | | |
|---|---|---|---|
| | L 1210 | B 16 | A 549 |
| Example 1 | 73.5 | 3.0 | 17.6 |
| Reference A | 7.8 | 5.1 | 30.5 |

-continued

| Test compounds | Cytotoxicity IC$_{50}$ (nM) | | |
|---|---|---|---|
| | L 1210 | B 16 | A 549 |
| Reference B | 24.3 | 6.8 | 39.4 |

The cytotoxicity of the product of Example 1 of the present invention is greater for lines B 16 and A 549 than for line L 1210, which indicates better in vitro activity for solid tumors. For those two lines (B 16 and A 549), the product of Example 1 of the present invention is more cytotoxic than reference products A and B.

B/In vivo Activity: Anti-tumor Activity

Line P 388 (murine leukaemia) is supplied by The National Cancer Institute (Frederick, USA). The tumor cells ($10^6$ cells) are inoculated on day 0 into the peritoneal cavity of female BDF1 mice (Iffa-Credo, France) weighing from 18 to 20 g (groups of 6 or 7 animals).

The products are administered intravenously on day 1 or on days 1, 5 and 9 at the doses indicated.

The anti-tumor activity is expressed as % T/C:

$$\% \ T/C = \frac{\text{Median survival time of the treated animals}}{\text{Median survival time of the control animals}} \times 100$$

The animals surviving at 60 days (long-term survivors) are indicated.

Line B 16 (murine melanoma) is supplied by The National Cancer Institute (Frederick, USA). The tumor is maintained by successive subcutaneous grafts of tumor fragments. On day 0, the tumors are broken up and homogenised in 0.9% NaCl (1 g, of tumor in 10 ml) and 0.5 ml of the homogenate is injected into the peritoneal cavity of each BDF1 mouse. The products are administered intraperitoneally at the doses indicated once a day for 9 days ($D_{1-9}$).

The anti-tumor activity is expressed as % T/C, as defined above. The animals surviving at 90 days (long-term survivors) are indicated.

Results

The product of Example 1 of the present invention is more potent than, and as active as, reference product A in the leukaemia P 388 model. The product of Example 1 of the present Application is very active in the melanoma B 16 model, at the optimum dose, it results in 3 long-term survivors whereas reference product A results in none. The product of Example 1 of the present Application is therefore very valuable against resistant solid tumors.

| | | | In vivo anti-tumour activity | | | |
|---|---|---|---|---|---|---|
| Tumour | Product | Schedule | Route | Optimum dose | % T/C | Long-term survivors/total no. of mice |
| P 388 i.p. | Example 1 | $D_1$ | i.v. | 10 mg/kg | 252 | 1/6 |
| | | $D_{1,5,9}$ | i.v. | 10 mg/kg | >582 | 3/6 |
| | Reference A | $D_1$ | i.v. | 80 mg/kg | 221 | 0/6 |
| | | $D_{1,5,9}$ | i.v. | 80 mg/kg | 320 | 2/6 |
| B 16 i.p. | Example 1 | $D_{1-9}$ | i.p. | 5 mg/kg | 429 | 3/7 |
| | Reference A | $D_{1-9}$ | i.p. | 10 mg/kg | 190 | 0/7 |

We claim:

1. A compound selected from those of formula I:

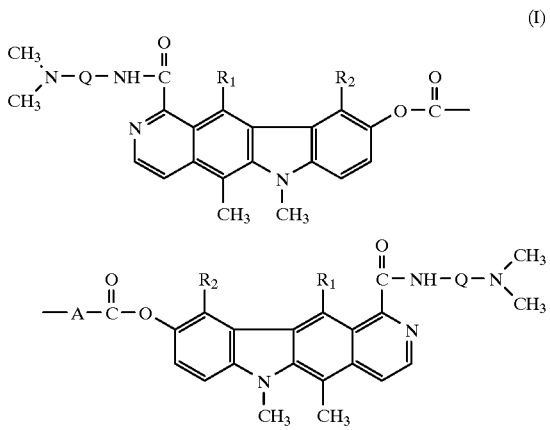

in which:

R$_1$ and R$_2$, which may be the same or different, are each selected from the group consisting of hydrogen and methyl;

A is selected from the group consisting of C$_1$–C$_{12}$ alkylene, and the same optionally including a C$_3$–C$_6$ saturated cycloalkyl or a saturated C$_3$–C$_6$ cycloalkyl; and Q is selected from the group consisting of linear and branched C$_1$–C$_8$ alkylene;

and their optical isomers, N-oxides and addition salts thereof with a pharmaceutically-acceptable acid.

2. A compound of claim 1 which is the bis[1-(2-dimethylaminoethylcarbamoyl)-5,6,11-trimethyl-6H-pyrido[4,3-b]carbazol-9-yl] ester of hexanedioic acid.

3. A method for treating a living animal body afflicted with leukemia, melanoma, or human pulmonary carcinoma, comprising the step of administering to the said living animal body an amount of a compound of claim 1 or 2 which is effective for the alleviation of the said disease.

4. A pharmaceutical composition, comprising as active ingredient an effective amount of at least one compound according to claim 1, in admixture or in association with one or more pharmaceutically-acceptable excipients or carriers.

5. A method for treating a living animal body afflicted with leukemia, melanoma, or human pulmonary carcinoma, comprising the step of administering to the said living animal body an amount of a compound of claim 2 which is effective for the alleviation of the said disease.

6. A pharmaceutical composition comprising as active ingredient an effective amount of at least one compound according to claim 2, in admixture or in association with one or more pharmaceutically-acceptable excipients or carriers.

* * * * *

UNITED STATES PATENT AND TRADEMARK OFFICE
CERTIFICATE OF CORRECTION

PATENT NO. : 5,958,938
DATED : Sep. 28, 1999
INVENTOR(S) : Claude Guillonneau, et al.

It is certified that error appears in the above-identified patent and that said Letters Patent is hereby corrected as shown below:

Title Page, [57] ABSTRACT, line 6(approx.):
"phar-maceutically acceptable" should read
-- pharmaceutically-acceptable --.

Column 3, line 47: "oryanic" should read -- organic --.

Column 3, line 50: Delete the "comma" after the word "using".

Column 4, line 55: The words "semiautoimated" and "calorimetric" should read -- semiautomated -- and -- colorimetric --.

Column 4, line 67: "-5,6-diiethyl-" should read -- -5,6-dimethyl- --.

Column 6, line 58: Insert a -- comma -- after the word "N-Oxides".

Signed and Sealed this

Twenty-fifth Day of April, 2000

Attest:

Q. TODD DICKINSON

*Attesting Officer*   *Director of Patents and Trademarks*